United States Patent
Xu et al.

(10) Patent No.: US 11,142,510 B2
(45) Date of Patent: *Oct. 12, 2021

(54) SYSTEM AND METHOD FOR CONTINUOUSLY PREPARING FURFURAL USING ACID-CONTAINING PENTOSE SOLUTION

(71) Applicant: ECO Environmental Energy Research Institute Limited, Hong Kong (CN)

(72) Inventors: Bin Xu, Hong Kong (CN); Kam Shing Siu, Hong Kong (CN); Junde Lu, Hong Kong (CN); Connie Hiu Ying Chow, Hong Kong (CN)

(73) Assignee: ECO Environmental Energy Research Institute Limited, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/894,564

(22) Filed: Jun. 5, 2020

(65) Prior Publication Data

US 2020/0369636 A1 Nov. 26, 2020

Related U.S. Application Data

(63) Continuation of application No. PCT/CN2018/117648, filed on Nov. 27, 2018.

(30) Foreign Application Priority Data

Dec. 6, 2017 (CN) .......................... 201711275961.3
Dec. 6, 2017 (CN) .......................... 201721684194.7

(51) Int. Cl.
   *C07D 307/50* (2006.01)
(52) U.S. Cl.
   CPC .................................. *C07D 307/50* (2013.01)
(58) Field of Classification Search
   CPC .................................................. C07D 307/50
   USPC .......................................................... 549/489
   See application file for complete search history.

(56) References Cited

U.S. PATENT DOCUMENTS

2013/0172583 A1   7/2013   Corbin et al.

FOREIGN PATENT DOCUMENTS

| CN | 101108838 A | 1/2008 |
|---|---|---|
| CN | 201482341 U | 5/2010 |
| CN | 104039772 A | 9/2014 |
| CN | 107235939 A | 10/2017 |
| CN | 107235940 A | 10/2017 |
| CN | 107805231 A | 3/2018 |
| CN | 107827847 A | 3/2018 |
| CN | 207877625 U | 9/2018 |
| CN | 208055237 U | 11/2018 |
| GB | 774809 | 5/1957 |

OTHER PUBLICATIONS

International Search Report and Written Opinion dated Mar. 6, 2019 in connection with International Application No. PCT/CN2018/117648, 16 pages.
First Office Action dated Oct. 16, 2020 in connection with Chinese Application No. 201711275961.3, 7 pages.
China Academic Journal Electronic Publishing House, "Sodium acetate recovery technology in furfural production", http://www.cnki.net, 1994-2020, 2 pages.
Second Office Action dated Mar. 10, 2021 in connection with Chinese Application No. 201711275961.3, 8 pages.
European Search Report dated Jun. 9, 2021 in connection with European Application No. 18885810.4, 4 pages.

*Primary Examiner* — Taofiq A Solola
(74) *Attorney, Agent, or Firm* — Baker & McKenzie LLP

(57) ABSTRACT

The present invention discloses a system and a method for continuously preparing furfural using an acid-containing pentose solution. The system comprises a stripping reaction column, a separation unit, and a purification unit. The method comprises a stripping reaction step, a separation step, and a purification step. The system and the method of the present invention can use a liquid inorganic acid as a catalyst, has a strong catalytic capability and a low reaction temperature, and is capable of treating low concentration sugar liquids. The present invention adopts heating through directly vapor stripping to rapidly carry away a generated furfural along with the vapor while reacting a pentose, avoiding side reactions of the furfural in an acidic liquid environment. The reaction process of the present invention does not require any extracting agent, and the furfural carried away along with the vapor is easy to separate after cooling. The whole process has a reasonable design, high furfural yields and low unit energy consumption.

16 Claims, 2 Drawing Sheets

SYSTEM AND METHOD FOR CONTINUOUSLY PREPARING FURFURAL USING ACID-CONTAINING PENTOSE SOLUTION

CROSS-REFERENCE TO RELATED APPLICATIONS

This application is a continuation application of International Application No. PCT/CN2018/117648 filed Nov. 27, 2018, which claims priority to Chinese Application No. 201711275961.3 filed Dec. 6, 2017 and claims priority to Chinese Application No. 201721684194.7 filed Dec. 6, 2017, the contents of all of which are hereby expressly incorporated by reference in their entirety, including the contents and teachings of any references contained therein.

TECHNICAL FIELD

The present invention belongs to the technical field of furfural production, in particular to a technique for continuously preparing furfural using an acid-containing pentose solution in a two-step process for preparing furfural.

BACKGROUND

Furfural (also known as furaldehyde) is an important chemical product and widely used in synthetic plastics, pharmaceuticals, pesticides and other industrial fields. The annual demand for furfural is enormous globally. The furfural can selectively extract unsaturated components from petroleum and vegetable oils, as well as aromatic components from lubricating oils and diesel oils. With the intensification of the energy crisis and environmental protection requirements, the use of renewable agricultural and forestry waste to produce high value-added furfural has received increasing attention.

At present, on the industrial scale, the sole method for obtaining furfural is still a hydrolysis method by taking corncob as a raw material. The furfural production technology can be further divided into a one-step method and a two-step method, depending on whether the pentosan hydrolysis and the dehydration/cyclization of the pentose monomer starting from corncob hemicellulose are carried out in the same reactor.

In the one-step method, the hemicellulose-containing raw material is placed into a hydrolysis pot. The hemicellulose is hydrolyzed to be pentose under a certain temperature and with acid catalysis, and the pentose is simultaneously dehydrated to form the furfural. The one-step method is widely used in the furfural industry because of its low investment in equipments and simple operation. However, the one-step method could lead to low furfural yield, large vapor consumption and serious environmental pollution because the raw materials are not heated uniformly.

The two-step method divides the hydrolysis reaction of hemicellulose and the dehydration reaction of pentose into two steps, which are respectively carried out in different equipments, and the reaction formula is as follows:

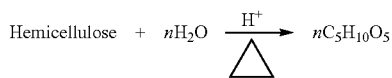

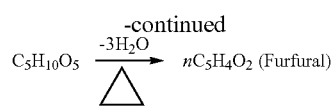

At present, in the first step, hemicellulose hydrolysis produces a high yield of pentose, but in the second step of the pentose dehydration/cyclization process, the furfural yield is low due to the decomposition reaction of the furfural itself and the polycondensation reaction of the reaction intermediate. Thus, how to reduce the decomposition reaction of furfural and polycondensation reaction in the pentose dehydration/cyclization step and thus increase the furfural yield is critical to the two-step method. Since developed countries such as Europe and the United States have already stopped furfural production, there are few researches and reports on furfural technology.

Patent application CN 103339119 A discloses a liquid phase dehydration reaction of xylose dissolved in a solvent by using a continuous tubular reactor without using a heterogeneous catalyst. In this method, however, the furfural as produced cannot leave the reaction system timely, so that the mutual polymerization reaction occurs between the furfural and the raw material xylose and the reaction intermediate, and the furfural is further degraded to form a ketone, and an aldehyde, etc., which reduces the selectivity of the xylose to form furfural.

Patent application CN 102690248 A discloses a pentose solution to form furfural in a system with an extractant through continuous countercurrent extraction. Although this method can remove the furfural from the acidic reaction environment timely and improve the selectivity of furfural, the extractant as used is expensive and has high toxicity and thus would complicate wastewater treatment and require a large amount of energy for recovery and recycling of the extractant, with complicated process operations and high investments in equipments.

Patent CN102584751 B introduces a process for preparing furfural by a reactive distillation method. The organic acid formic acid and acetic acid are used as catalysts in this patent. Due to the poor catalytic effect of the organic acids, higher reaction temperature and reaction pressure are required. The most important issue is that the reaction distillation column bottom provides heat by indirect heating. Since the pentose-containing solution usually contains salts and other sugar impurities, the surface of the heat exchanger is easy to coke when exchanging heat with the heat exchanger in an acidic environment, which causes the reaction not to proceed continuously.

SUMMARY

The present invention has been presented in view of the abovementioned problems in the prior art. The invention provides a system for continuously preparing furfural with an acid-containing pentose solution and also a method for continuously preparing furfural with an acid-containing pentose solution, which at least solves the problems of low furfural yield and production efficiency, many by-products, high production cost, and serious environmental pollution and the like in the prior art. It can effectively increase furfural yield and avoid the occurrence of side reactions as much as possible, with low unit energy consumption and environmental pollution.

According to an aspect of the present invention, a system for continuously preparing furfural with an acid-containing pentose solution is provided. The system comprises a stripping reaction column comprising, at the top, a vapor outlet and a first raw material inlet, and at the bottom, a stripping vapor inlet and an acid liquid outlet. The first raw material inlet is for receiving an acid-containing pentose solution of a first temperature as a raw material for performing a dehydration/cyclization reaction. The stripping vapor inlet is for receiving a stripping vapor of a second temperature. The vapor outlet is for supplying a furfural-containing vapor obtained from the reaction. The acid liquid outlet is for extracting an acid liquid from the bottom of the column. The system further comprises a separation unit connected to the vapor outlet for neutralizing the acid in the furfural-containing vapor and separating the resulting salt from the furfural-containing vapor to provide a furfural-containing vapor with a reduced acid content; and a purification unit for purifying the resulting furfural.

According to another aspect of the present invention, a method for continuously preparing furfural with an acid-containing pentose solution is provided. The method comprises: a stripping reaction step, which is performed by using a stripping reaction column, so that a acid-containing pentose solution of a first temperature enters the stripping reaction column from the top, and a stripping vapor of a second temperature enters the stripping reaction column from the bottom, the stripping vapor being in countercurrent contact with the pentose solution which is subject to dehydration/cyclization reaction, so as to obtain a furfural-containing vapor and an acid liquid; a separation step, wherein the furfural-containing vapor is neutralized and the resulting salt is separated from the furfural-containing vapor to provide a furfural-containing vapor with a reduced acid content; and a purification step, wherein the resulting furfural is purified.

The present invention can use a liquid inorganic acid as a catalyst, with strong catalytic ability and low reaction temperature. The present invention is also capable of treating low concentration sugar solution as compared to solvent extraction. The present invention adopts a vapor counterflow stripping reaction process, into which no extractant is added, and the acid-containing pentose solution contacts the vapor from top to bottom. While the furfural is generated with the dehydration/cyclization reaction, the furfural as generated is brought out by the vapor simultaneously, thus avoiding the side reaction of furfural due to being in a liquid acidic environment for a long time. The bottom of the stripping reaction column of the present invention is free of a reboiler, and the top thereof is free of a reflux unit. Since the pentose-containing solution usually contains salts and other sugar impurities, the heat exchange in the reboiler in an acidic environment easily causes the surface of the reboiler to coke and thereby the reaction could not proceed continuously, while heating with vapor directly stripping avoids this problem and saves equipment investment. At the same time, heating with vapor directly stripping can also control the residence time of the liquid by adjusting the amount of vapor to avoid overreaction. The invention simplifies the production process of furfural. The subsequent separation and purification of furfural is simple and easy. The whole process design is reasonable. The furfural yield is 10% to 30% higher and the unit energy consumption is 10% to 20% lower compared to the traditional one-step process.

BRIEF DESCRIPTION OF THE DRAWINGS

The following drawings of the present invention are hereby incorporated as part of the invention for the understanding of the invention. The embodiments and description of the invention have been presented in the drawings in order to explain the principles of the invention.

DETAILED DESCRIPTION

In the following description, numerous specific details are set forth in order to provide a more thorough understanding of the present invention. However, it will be apparent to those skilled in the art that the present invention may be implemented without one or more of these details. In other instances, some of the technical features well known in the art have not been described so as not to confuse with the present invention.

Figure 1:
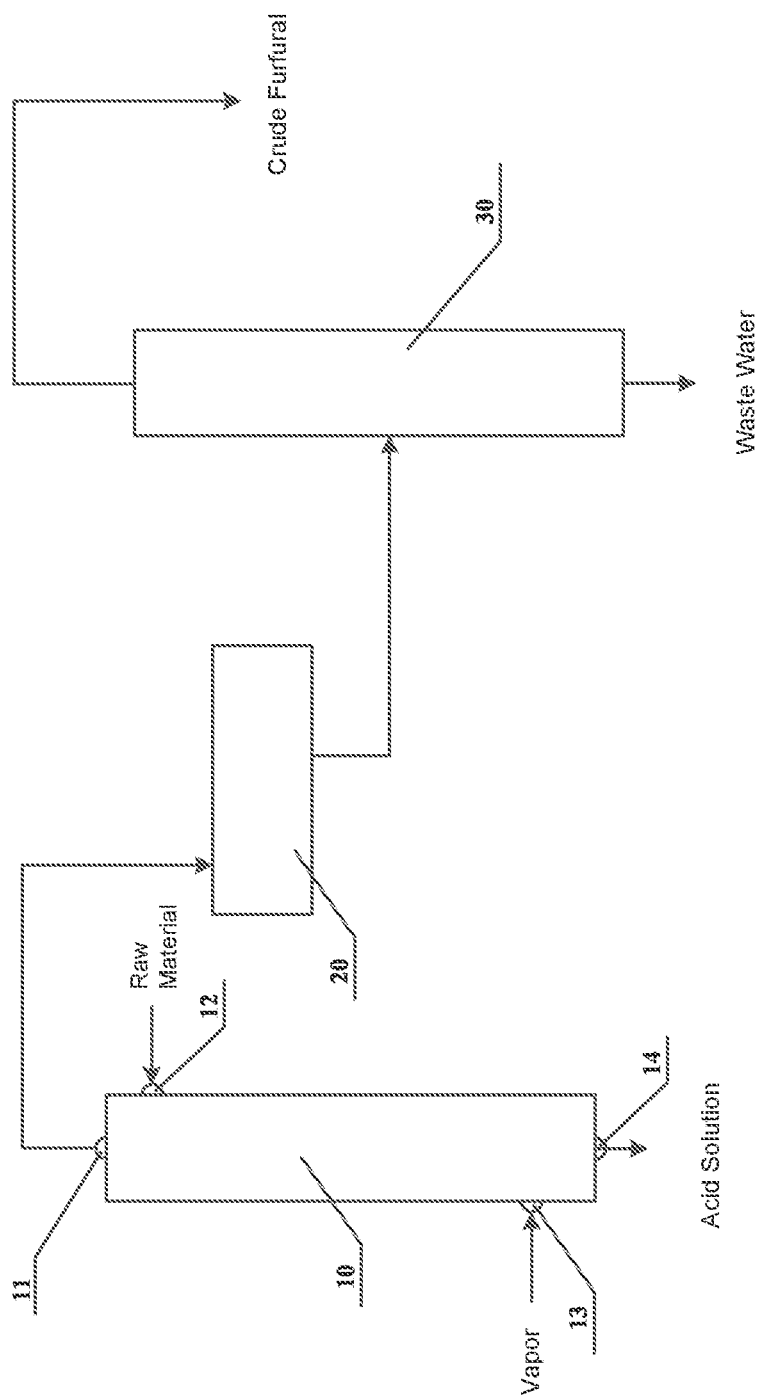
FIG. 1 is a schematic view of a system for continuously preparing furfural with an acid-containing pentose solution according to an embodiment of the present invention.

FIG. 1 schematically illustrates an embodiment in accordance with the present invention.

As shown in FIG. 1, it is a system for continuously preparing furfural with an acid-containing pentose solution, comprising a stripping reaction column 10, a vapor outlet 11, a first raw material inlet 12, a stripping vapor inlet 13, an acid solution outlet 14, a separation unit 20, and a purification unit 30.

The device can continuously produce furfural using an acid-containing pentose solution with the following process.

The acid-containing pentose solution as heated by a heater to a first temperature enters the stripping reaction column 10 from the first raw material inlet 12 at the top of the column 10, and a stripping vapor of a second temperature enters the stripping reaction column 10 from the stripping vapor inlet 13 at the bottom of the column 10. The acid-containing pentose solution is subject to a dehydration/cyclization reaction in the stripping reaction column 10 to generate furfural, with the acid as a catalyst. Subsequently, the generated furfural is extracted from the vapor outlet 11 at the top of the stripping reaction column 10, and the acid solution is extracted from the acid solution outlet 14 at the bottom of the stripping reaction column 10. The extracted furfural-containing vapor enters the separation unit 20 connected to the stripping reaction column 10, and the acid in the furfural-containing vapor is neutralized in the separation unit 20 to obtain a furfural-containing vapor with a reduced acid content, which enters the purification unit 30 connected to the separation unit 20 and is purified in the purification unit 30.

In a preferred embodiment, the separation unit 20 may further comprise a filtration device, preferably a ceramic filter, for filtering the furfural-containing vapor with a reduced acid content to further remove impurities from the furfural-containing vapor. The use of the filtration device can effectively reduce the amount of furfural mud generated in the subsequent furfural refining process and prolong the service life of the reboiler and heat exchange unit of the preliminary distillation column.

In a preferred embodiment, the system for preparing furfural may further comprise a heat exchange unit comprising: a raw material passage and a furfural passage. The raw material passage receives the acid-containing pentose solution as a raw material, and the furfural passage receives the furfural-containing vapor from the separation unit 20. The acid-containing pentose solution and the furfural-containing vapor pass through the raw material passage and the furfural passage, respectively. The passages are isolated from each other but enable the heat exchange between the acid-containing pentose solution and the furfural-containing vapor. The acid-containing pentose solution and the furfural solution as obtained after heat exchange are respectively delivered to the stripping reaction column 10 and the purification unit 30. The heat exchange unit can effectively utilize the heat of the furfural-containing vapor to increase the temperature of the acid-containing pentose solution, so that the acid-containing pentose solution can reach the reaction temperature faster and heat waste is avoided.

In a preferred embodiment, the purification unit 30 may comprise a preliminary distillation column having a preliminary distillation column feed port at the middle, a preliminary distillation column vapor outlet and an aqueous phase liquid inlet at the top, and a reboiler vapor inlet and an preliminary distillation column bottom liquid outlet at the bottom; and a furfural solution heat exchanger, wherein the furfural solution is cooled to a third temperature by the furfural solution heat exchanger and enters the preliminary distillation column through the preliminary distillation column feed port. A preliminary distillation column reboiler is provided at the bottom of the preliminary distillation column, and a reflux unit is provided at the top of the column. The reflux unit comprises a preliminary distillation column condenser and a preliminary distillation column liquid separation tank. After exchanging heat through the preliminary distillation column reboiler, a part of the bottom liquid becomes reboiler vapor and returns to the preliminary distillation column via the reboiler vapor inlet. The preliminary distillation column condenser is connected to the preliminary distillation column vapor outlet for condensing the purified furfural-containing vapor to a condensate of a fourth temperature. The preliminary distillation column liquid separation tank is connected to the preliminary distillation column condenser, for receiving the condensate, performing liquid separation to obtain an aqueous phase liquid and an oil phase liquid, returning the aqueous phase liquid to the preliminary distillation column through the aqueous liquid inlet, and outputting the oil phase liquid as a crude furfural product.

In a preferred embodiment, the separation unit 20 may comprise an alkaline solution inlet to input an alkali solution for neutralization to neutralize the acid in the furfural-containing vapor, thereby preventing the acid from decomposing or polycondensing the furfural in a subsequent treatment.

In a preferred embodiment, the separation method of the separation unit 20 may be one or more of inertial separation, filtration separation, and centrifugal separation. The present invention preferably employs a cyclone separator belonging to a centrifugal separation method for separating salt and solid impurities from the furfural-containing vapor to provide a furfural-containing vapor with a reduced acid content. The cyclone separator has the advantages of simple structure, convenient operation, high temperature resistance and long service life.

In a preferred embodiment, the furfural preparing system may also comprise an acid solution heat exchanger for receiving the acid solution extracted from the acid solution outlet 14 at the bottom of the stripping reaction column 10 and conducting heat recovery.

In a preferred embodiment, the purification unit 30 may further comprise a refining unit for performing refining of the crude furfural product by dehydration and removal of light components to obtain a product furfural.

In a preferred embodiment, the purification unit 30 may further comprise a wastewater evaporator for evaporating and reusing a portion of the liquid discharged from the bottom of the preliminary distillation column.

In a preferred embodiment, the first temperature may be set to be 80° C. to 155° C., and the second temperature may be set to be 150° C. to 220° C. The stripping reaction column 10 may be set to have a temperature of 140° C. to 210° C. at the top and a temperature of 150° C. to 220° C. at the bottom, and have a pressure of 0.26 MPa to 2.2 MPa (gauge pressure) at the top and a pressure of 0.37 MPa to 2.2 MPa (gauge pressure) at the bottom. The temperature and pressure of the stripping reaction column 10 can be adjusted and set by adjusting the temperature and pressure of the feeding.

In a preferred embodiment, the third temperature may be set to be 20° C. to 100° C., and the fourth temperature may be set to be 30° C. to 90° C. The preliminary distillation column may be set to have a temperature of 100° C. to 115° C. at the top and a temperature of 120° C. to 160° C. at the bottom, and have a pressure of 0 MPa to 0.03 MPa (gauge pressure) at the top and a pressure of 0 MPa to 0.35 MPa (gauge pressure) at the bottom. The temperature and pressure of the preliminary distillation column can be adjusted and set by adjusting the temperature and pressure of the feeding, the reboiling ratio, and the reflux ratio, and the like.

In a preferred embodiment, the bottom of the stripping reaction column is free of a reboiler, and the top thereof is free of a reflux unit.

Figure 2:
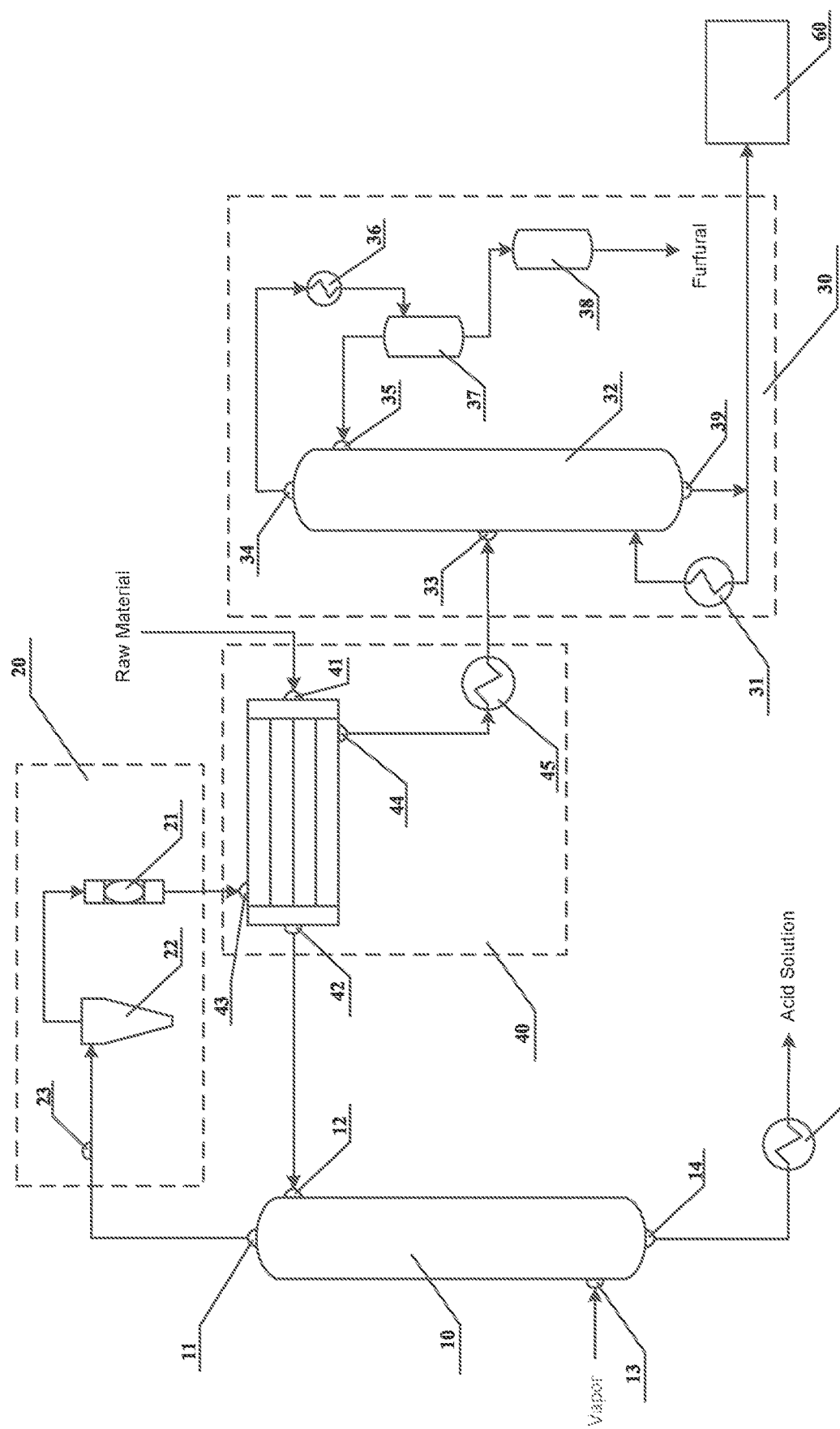
FIG. 2 is a schematic view of a system for continuously preparing furfural with an acid-containing pentose solution according to another embodiment of the present invention.

FIG. 2 schematically illustrates a preferred embodiment in accordance with the present invention. According to the embodiment, a system for continuously preparing furfural with an acid-containing pentose solution is provided. It comprises a stripping reaction column 10, a vapor outlet 11, a first raw material inlet 12, a stripping vapor inlet 13, an acid solution outlet 14, a separation unit 20, a ceramic filter 21, a cyclone separator 22, an alkaline solution input port 23, a purification unit 30, a preliminary distillation column reboiler 31, a preliminary distillation column 32, a preliminary distillation column feed port 33, a preliminary distillation column vapor outlet 34, an aqueous phase liquid inlet 35, a preliminary distillation column condenser 36, a preliminary distillation column liquid separation tank 37, a refining unit 38, a preliminary distillation column bottom liquid outlet 39, a heat exchange unit 40, a second raw material inlet 41, a raw material outlet 42, a furfural inlet 43, a furfural outlet 44, a furfural solution heat exchanger 45, an acid solution heat exchanger 50, and a wastewater evaporator 60.

The device can continuously prepare furfural with the following process.

The stripping vapor of the second temperature enters the column from the stripping vapor inlet 13 at the bottom of the stripping reaction column 10, and the acid-containing pentose solution of the first temperature enters the column from the first raw material inlet 12 at the top of the stripping reaction column 10. The acid-containing pentose solution is subject to a dehydration/cyclization reaction in the stripping reaction column 10 to generate furfural, with the acid as a catalyst. Subsequently, the generated furfural is extracted from the vapor outlet 11 at the top of the stripping reaction column 10, and the acid solution is extracted from the acid liquid outlet 14 at the bottom of the stripping reaction column 10.

The extracted furfural-containing vapor enters the separation unit 20 connected to the stripping reaction column 10. The alkali solution enters the separation unit 20 from the alkaline solution input port 23 to neutralize the acid in the furfural-containing vapor, and the vapor then enters the cyclone separator 22 to separate the salt obtained by neutralization from the furfural-containing vapor to generate a furfural-containing vapor with a reduced acid content. The furfural-containing vapor with the reduced acid content then passes through the ceramic filter 21 to further remove impurities in the vapor, thereby preventing the vapor from coking in the subsequent heat exchange process and reducing the production of furfural mud.

The furfural-containing vapor enters the heat exchange unit 40 through the furfural inlet 43, and the acid-containing pentose solution enters the heat exchange unit 40 through the second raw material inlet 41. The acid-containing pentose solution and the furfural-containing vapor pass through the raw material passage and the furfural passage, respectively. The passages are isolated from each other but enable the heat exchange between the acid-containing pentose solution and the furfural-containing vapor. The acid-containing pentose solution after heat exchange enters the stripping reaction column 10 through the first raw material inlet 12 after being output from the raw material outlet 42. The furfural solution obtained after heat exchange is output from the furfural outlet 44.

The furfural solution then enters the purification unit 30 connected to the separation unit 20. First, the furfural solution is cooled to a third temperature through the furfural solution heat exchanger 45 and then enters the preliminary distillation column 32 from the preliminary distillation column feed port 33, and the purified furfural-containing vapor is extracted from the preliminary distillation column vapor outlet 34 at the top of the column after the furfural solution is purified in the preliminary distillation column 32. Subsequently, the purified furfural-containing vapor enters the preliminary distillation column condenser 36 to be cooled to a fourth temperature and is then delivered to the preliminary distillation column liquid separation tank 37 in which an aqueous phase liquid and an oil phase liquid are obtained from liquid separation. The aqueous phase liquid flows back to the preliminary distillation column 32 through the aqueous liquid inlet 35, and the oil phase liquid is output as the crude furfural product. A portion of the bottom liquid extracted from the preliminary distillation column bottom liquid outlet 39 becomes reboiler vapor after heat exchange with the primary distillation column reboiler 31 and returns to the preliminary distillation column 32 through the reboiler vapor inlet, and the remaining portions of the bottom liquid are extracted as wastewater.

In a preferred embodiment, the system may further comprise an acid solution heat exchanger 50 for receiving the acid solution flowing from the acid solution outlet 14 and performing heat recovery.

In a preferred embodiment, the purification unit 30 may further comprise a refining unit 38 for performing refining of the crude furfural product by dehydration and removal of light components of so as to obtain a product furfural.

In a preferred embodiment, the system may also comprise a wastewater evaporator 60 for evaporating and reusing a portion of the bottom liquid of the preliminary distillation column 32.

In a preferred embodiment, the first temperature may be set to be 80° C. to 155° C., and the second temperature may be set to be 150° C. to 220° C. The stripping reaction column 10 may be set to have a temperature of 140° C. to 210° C. at the top and a temperature of 150° C. to 220° C. at the bottom, and have a pressure of 0.26 MPa to 2.2 MPa (gauge pressure) at the top and a pressure of 0.37 MPa to 2.2 MPa (gauge pressure) at the bottom. The temperature and pressure of the stripping reaction column 10 can be adjusted and set by adjusting the temperature and pressure of the feeding.

In a preferred embodiment, the third temperature may be set to be 20° C. to 100° C., and the fourth temperature may be set to be 30° C. to 90° C. The preliminary distillation column 32 may be set to have a temperature of 100° C. to 115° C. at the top and a temperature of 120° C. to 160° C. at the bottom, and have a pressure of 0 MPa to 0.03 MPa (gauge pressure) at the top and a pressure of 0 MPa to 0.35 MPa (gauge pressure) at the bottom. The temperature and pressure of the preliminary distillation column 82 can be adjusted and set by adjusting the temperature and pressure of the feeding, the reboil ratio, and the reflux ratio, and the like.

The present invention also relates to a method for continuously preparing furfural with an acid-containing pentose solution, the method comprising: a stripping reaction step which is performed by using a stripping reaction column, so that the acid-containing pentose solution of a first temperature enters the stripping reaction column from the top, and a stripping vapor of a second temperature enters the stripping reaction column from the bottom, the stripping vapor being in countercurrent contact with the pentose solution which is subject to a dehydration/cyclization reaction, thereby obtaining a furfural-containing vapor and an acid solution; a separation step, wherein the furfural-containing vapor is neutralized and the resulting salt is separated from the furfural-containing vapor to provide a furfural-containing vapor with a reduced acid content; and a purification step wherein the resulting furfural is purified.

In a preferred embodiment, the separation step may further comprise filtering the furfural-containing vapor with the reduced acid content to provide a filtered furfural-containing vapor.

In a preferred embodiment, the method may further comprise a heat exchange step, wherein an isolated heat exchange is carried out between the furfural-containing vapor from the separation step and the acid-containing pentose solution having a temperature lower than the first temperature, so that the acid-containing pentose solution reaches the first temperature to serve as a raw material for the stripping reaction step and a furfural solution is provided.

In a preferred embodiment, the purification step comprises rectification with a preliminary distillation column. The furfural solution is cooled to a third temperature and enters the preliminary distillation column for rectification. The purified furfural-containing vapor obtained from rectification is condensed to a fourth temperature and separated. The obtained aqueous phase liquid returns to the preliminary distillation column, and the oil phase liquid is output as a crude furfural product. A portion of the bottom liquid obtained from the rectification exits the preliminary distillation column and reenters therein as reboiler vapor after heat exchange with the preliminary distillation column reboiler.

In a preferred embodiment, the furfural-containing vapor can be neutralized with an alkaline solution in the separation step.

In a preferred embodiment, the salt can be separated from the furfural-containing vapor using a cyclone separator in the separation step to provide a furfural-containing vapor with a reduced acid content.

In a preferred embodiment, the acid solution obtained from the stripping reaction step is subject to heat recovery.

In a preferred embodiment, the method may further comprise a refining step, wherein the crude furfural product is refined by dehydration and removal of light components to obtain a product furfural.

In a preferred embodiment, the method may further comprise evaporating and reusing a portion of the bottom liquid exiting the preliminary distillation column.

In a preferred embodiment, the first temperature may be 80° C. to 155° C., and the second temperature may be 150° C. to 220° C. The stripping reaction column may have a temperature of 140° C. to 210° C. at the top and a temperature of 150° C. to 220° C. at the bottom, and have a pressure of 0.26 MPa to 2.2 MPa (gauge pressure) at the top and a pressure of 0.37 MPa to 2.2 MPa (gauge pressure) at the bottom. The temperature and pressure of the stripping reaction column can be adjusted and set by adjusting the temperature and pressure of the feeding.

In a preferred embodiment, the third temperature may be 20° C. to 100° C., and the fourth temperature may be 30° C. to 90° C. The preliminary distillation column may have a temperature of 100 to 115° C. at the top and a temperature of 120° C. to 160° C. at the bottom, and have a pressure of 0 MPa to 0.03 MPa (gauge pressure) at the top and a pressure of 0 MPa to 0.35 MPa (gauge pressure) at the bottom. The temperature and pressure of the preliminary distillation column can be adjusted and set by adjusting the temperature and pressure of the feeding, the reboil ratio, and the reflux ratio, and the like.

In a preferred embodiment, the bottom of the stripping reaction column is free of a reboiler, and the top thereof is free of a reflux unit.

In a preferred embodiment, the acid may be selected from at least one of sulphur acid, hydrochloric acid, phosphoric acid or nitric acid, and the acid has a concentration of 0.1% to 10% by weight, preferably 1% to 5% by weight, most preferably 2% to 4% by weight.

In a preferred embodiment, the pentose solution has a sugar concentration of 1 g/l to 100 g/l, preferably 1 g/l to 50 g/l, most preferably 5 g/l to 30 g/l.

The above method of the present invention can be carried out by using the system of the present invention or a system with other configurations as long as the effects of the invention can be achieved.

Example

The system as shown in FIG. 2 is used to continuously prepare furfural with an acid-containing pentose solution.

Wherein, a pentose solution with a pentose concentration of 5 g/l is used as a pentose raw material solution, and sulphur acid is added thereto as a catalyst, so that the sulphur acid in the pentose solution has a concentration of 4% by weight. The acid-containing pentose solution is heated to 150° C. via the heat exchange unit 40 and then introduced into the stripping reaction column 10 from the first raw material inlet 12. At the same time, the stripping vapor with a temperature of 180° C. is fed from the stripping vapor inlet 13 into the stripping reaction column 10. The ascending stripping vapor is brought into countercurrent contact with the pentose solution. The pentose solution is heated to about 170° C. to carry out a dehydration/cyclization reaction in the reaction column 10. The generated furfural enters the stripping vapor and is extracted out from the vapor outlet 11 at the top of the stripping reaction column 10 at 170° C. (with a pressure of 0.74 MPa at the top of the column), and the extracted furfural-containing vapor contains 8% by weight of furfural.

The extracted furfural-containing vapor is output to the separation unit 20 and subject to vapor phase neutralization with a 12% by weight of sodium carbonate solution. The resulting salt is separated from the furfural-containing vapor by a cyclone separator 22 so as to obtain a furfural-containing vapor with a reduced acid content. The furfural-containing vapor then enters the ceramic filter 21 and after filtration enters the heat exchange unit 40.

In the heat exchange unit 40, the filtered furfural-containing vapor is subject to heat exchange with the acid-containing pentose solution to obtain a furfural solution with a temperature of 170° C.

The furfural solution enters the purification unit 30, and after being further cooled to 85° C. by the furfural solution heat exchanger 45, it then enters the preliminary distillation column 32 from the preliminary distillation column feed port 33. After purification, the crude furfural vapor is taken out from the preliminary distillation column vapor outlet 34, and enters the preliminary distillation column liquid separation tank 37 after being condensed to 80° C. by the preliminary distillation column condenser 36. The aqueous phase liquid and the oil phase liquid are obtained by liquid separation, wherein the aqueous phase liquid contains an aldehyde concentration of 6% by weight, and the oil phase liquid contains 8% by weight of water.

The aqueous phase liquid returns from the top of the preliminary distillation column liquid separation tank 37 and enters the preliminary distillation column 32 from the aqueous phase liquid inlet 35. The oil phase liquid is output as a crude furfural product and enters a crude furfural storage tank.

The crude furfural product can be used as a product furfural after subsequent refining of dehydration and removal of light components. The furfural yield is 88% (relative to the theoretical yield of a pentose solution of 5 g/l).

In addition, the acid-containing liquid extracted from the acid liquid outlet 14 at the bottom of the stripping reaction column 10 has a temperature of 175° C., and may be cooled to 120° C. for recycling after heat is recovered by the acid liquid heat exchanger 50. The preliminary distillation column reboiler 31 is heated by vapor. A portion of the bottom liquid extracted from the preliminary distillation column bottom liquid outlet 39 becomes reboiler vapor after exchanging heat with the preliminary distillation column reboiler 31, and returns to the preliminary distillation column 32 via the reboiler vapor inlet. The remaining portions of the bottom liquid are extracted as wastewater. The extracted wastewater can enter the wastewater evaporator 60 and be recycled after secondary evaporation.

The present invention has been described by the above embodiments, but it is to be understood that the foregoing embodiments are only for the purpose of illustration and description but are not intended to limit the invention within the scope of the embodiments as described. In addition, those skilled in the art should understand that the present invention is not limited to the above embodiments. Many variations and modifications can still be made according to the teachings of the present invention. These variations and modifications fall within the scope of the present invention as defined by the appended claims and their equivalents.

What is claimed is:

1. A method for continuously preparing furfural using an acid-containing pentose solution, the method comprising:
   a stripping reaction step, which is performed using a stripping reaction column, wherein an acid-containing pentose solution of a first temperature enters the stripping reaction column from the top; a stripping vapor of a second temperature enters the stripping reaction column from the bottom; the stripping vapor is in countercurrent contact with the pentose solution, which is subject to a dehydration/cyclization reaction so as to obtain a furfural-containing vapor and an acid solution;

a separation step, wherein the furfural-containing vapor is neutralized and the resulting salt is separated from the furfural-containing vapor to provide a furfural-containing vapor with a reduced acid content; and a purification step, wherein the resulting furfural is purified.

2. The method according to claim 1, wherein the separation step further comprises filtering the furfural-containing vapor with the reduced acid content to provide a filtered furfural-containing vapor.

3. The method according to claim 1 or 2, wherein the method further comprises a heat exchange step, wherein the furfural-containing vapor from the separation step performs an isolated heat exchange with the acid-containing pentose solution with a temperature lower than the first temperature, so that the acid-containing pentose solution reaches the first temperature as a raw material for the stripping reaction step, and a furfural solution is provided.

4. The method according to claim 3, wherein the purification step comprises rectification with a preliminary distillation column; wherein the furfural solution is cooled to a third temperature through heat exchange and enters the preliminary distillation column for rectification; the purified furfural-containing vapor obtained from the rectification is condensed to a fourth temperature and separated; an aqueous phase liquid obtained from liquid separation is returned to the preliminary distillation column, and an oil phase liquid obtained from liquid separation is output as a crude furfural product; a portion of the bottom liquid obtained from the rectification exits the preliminary distillation column and reenters therein as reboiler vapor after exchanging heat with the preliminary distillation column reboiler.

5. The method according to claim 1, wherein the furfural-containing vapor is neutralized with an alkali solution in the separation step.

6. The method according to claim 1, wherein the salt is separated from the furfural-containing vapor using a cyclone separator in the separation step to provide the furfural-containing vapor with a reduced acid content.

7. The method according to claim 1, wherein the acid solution obtained from the stripping reaction step is subject to heat recovery.

8. The method according to claim 4, wherein the purification step further comprises a refining step, wherein the crude furfural product is subject to refining by dehydration and removal of light components to obtain a product furfural.

9. The method according to claim 4, wherein the purification step further comprises evaporating and reusing remaining portion of the bottom liquid exiting the preliminary distillation column.

10. The method according to claim 1, wherein the first temperature is 80° C. to 155° C.; the second temperature is 150° C. to 220° C.; the stripping reaction column top temperature is 140° C. to 210° C. and the stripping reaction column bottom temperature is 150° C. to 220° C.

11. The method according to claim 1, wherein the stripping reaction column top pressure is 0.26 MPa to 2.2 MPa (gauge pressure) and the stripping reaction column bottom pressure is 0.37 MPa to 2.2 MPa (gauge pressure).

12. The method according to claim 4, wherein the third temperature is 20° C. to 100° C.; the fourth temperature is 30° C. to 90° C.; the preliminary distillation column top temperature is 100° C. to 115° C. and the preliminary distillation column bottom temperature is 120° C. to 160° C.

13. The method according to claim 4, wherein the preliminary distillation column top pressure is 0 MPa to 0.03 MPa (gauge pressure) and the preliminary distillation column bottom pressure is 0 MPa to 0.35 MPa (gauge pressure).

14. The method according to claim 1, wherein the bottom of the stripping reaction column is free of a reboiler, and the top thereof is free of a reflux unit.

15. The method according to claim 1, wherein the acid is selected from at least one of sulphur acid, hydrochloric acid, phosphoric acid or nitric acid, and the acid has a concentration of 0.1% to 10% by weight.

16. The method according to claim 1, wherein the pentose solution has a sugar concentration of 1 g/l to 100 g/l.

* * * * *